United States Patent [19]
Kleeberg

[11] Patent Number: 5,695,763
[45] Date of Patent: Dec. 9, 1997

[54] METHOD FOR THE PRODUCTION OF STORAGE STABLE AZADIRACHTIN FROM SEED KERNELS OF THE NEEM TREE

[75] Inventor: Hubertus Kleeberg, Lahnau, Germany

[73] Assignee: Trifolio-M GmbH, Herstellung Und Vertrieb, Lahnau, Germany

[21] Appl. No.: 601,488

[22] Filed: Feb. 14, 1996

Related U.S. Application Data

[63] Continuation of Ser. No. 122,466, filed as PCT/DE92/00220 filed March 14, 1992, abandoned.

[30] Foreign Application Priority Data

Mar. 22, 1991 [DE] Germany ............................ 41 09 473.5

[51] Int. Cl.$^6$ .................... A01N 43/00; A01N 65/00; C07D 313/00
[52] U.S. Cl. .................... 424/195.1; 514/783; 549/354; 424/405
[58] Field of Search ............................ 424/195.1, 405; 514/783; 549/354

[56] References Cited

U.S. PATENT DOCUMENTS

| | | | |
|---|---|---|---|
| 4,556,562 | 12/1985 | Larson | 424/195.1 |
| 4,943,434 | 7/1990 | Lidert | 424/195.1 |
| 4,946,681 | 8/1990 | Walter | 424/195.1 |
| 5,001,146 | 3/1991 | Carter et al. | 514/453 |
| 5,001,149 | 3/1991 | Klocke et al. | 514/468 |
| 5,047,242 | 9/1991 | Klocke et al. | 424/195.1 |
| 5,110,591 | 5/1992 | Williams | 424/195.1 |
| 5,124,349 | 6/1992 | Carter et al. | 514/453 |
| 5,420,318 | 5/1995 | Lidert et al. | 554/193 |

FOREIGN PATENT DOCUMENTS

| | | |
|---|---|---|
| 0405291 | 1/1991 | European Pat. Off. . |
| 0405701 | 1/1991 | European Pat. Off. . |
| 0436257 | 7/1991 | European Pat. Off. . |
| 3702175 | 1/1987 | Germany . |

OTHER PUBLICATIONS

Chemical Abstracts (1984), CA 103(25):208833b Feuerhake, K.J. "Effectiveness and Selectivity of Technical Solvents for the Extraction of Neem Seed Components With Insecticidal Activity", Schriftenr. GTZ (1984) 161, 103–13.

Chemical Abstracts (1986), CA 105(3):20497g "The Effect of Various Extracts of Neem Seed Kernel on *Liriomyza trifolii* (Burgess) (Diptera: Agromyzidae)", Z. Pflanzenkrankh. Pflanzenschutz (1986) 93(2), 146–52.

Chemical Abstracts (1984), CA 103(23): 191415s K.R.S. Ascher et al. "Neem Seed Kernel Extract as an Inhibitor of Growth and Fecundity in *Spodoptera littoralis*", Schriftenr. GTZ (1984) 161, 331–44.

Chemical Abstracts (1990), CA 114(19):180294. Paul B. Tanzubil et al. "Effects of Azadirachtin and Aqueous Neem Seed Extracts on Survival, Growth and Development of the African Armyworm, Spodoptera Exempta", Crop Prot. (1990) 9(5), 383–6.

*Primary Examiner*—Kathleen K. Fonda
*Attorney, Agent, or Firm*—Flynn, Thiel, Boutell & Tanis, P.C.

[57] ABSTRACT

Azadirachtin is effectively recovered from the seeds of the neem tree by crushing the seeds, extracting azadirachtin from the crushed seeds with water and then either extracting azadirachtin from the water using a non-aqueous solvent which is not miscible with water and has a higher solubility of azadirachtin than water or a surfactant having a turbidity temperature between 20° and 80° C. The concentrated azadirachtin is easily recovered from the second extraction solution and shows high activity as an insecticide.

19 Claims, No Drawings

5,695,763

METHOD FOR THE PRODUCTION OF STORAGE STABLE AZADIRACHTIN FROM SEED KERNELS OF THE NEEM TREE

This application is a continuation of U.S. patent application Ser. No. 08/122,466, filed Dec. 22, 1993, now abandoned, which is a U.S. national stage entry under 35 U.S.C. 371 of PCT/DE92/00220, filed Mar. 14, 1992.

FIELD OF THE INVENTION

The invention concerns a method for the production of a storage stable azadirachtin-rich insecticide from components, especially the seeds of the neem tree, in which the components are reduced to small pieces and, to these crushed components, a solvent is added which extracts azadirachtin from the components, after which the azadirachtin is concentrated in the solvent.

BACKGROUND OF THE INVENTION

Several investigations have shown that one can proceed from the fact that amongst the ingredients of different parts, especially of the fruits, of the neem tree (azadirachta indica A. Juss), those with excellent properties for an environmentally sound plant protection against insect pests are present. In this connection, azadirachtin belongs to the most potent and abundant (approximately 1 to 20 g/(kg dried seed kernels)) substances in the fruits of the neem tree.

The dried seeds of the neem tree have already been used for the production of insecticides, for example the method according to U.S. Pat. No. 4,556,562. In this procedure, ingredients, which are soluble in ethanol, are extracted with this alcohol at 80° C. After evaporation of the alcohol, the residue may be formulated with a surfactant and/or water. With this known extraction procedure, as well as with other known extraction methods in which organic solvents are used, the solvent has to be evaporated in order to obtain a solid concentrate of the active compounds. All known procedures, which yield a product having a low oil content, require the application of several laborious purification steps (like extraction, concentration). In spite of this, the azadirachtin content is only between a few to about 35% if not even more sophisticated separation techniques, like chromatographic methods, are applied.

In this connection, the economic separation of the oil is a special problem. According to the extraction methods known at present, the oil is either separated before or after the isolation of the azadirachtin-rich fraction.

The oil may, for example, be removed by extraction with hydrocarbons (like petrolether, hexane) or by pressing of the oil, during which a temperature increase of the neem material occurs, which may lead to a severe decomposition of azadirachtin and consequently more or less dramatic losses in the active ingredients to be isolated.

The crude extract obtained by extraction of ground neem kernels with organic solvents like alcohols, ketones or halogenated hydrocarbons is frequently freed from the oil by shaking it with hydrocarbons (like petrolether, Hexane) after it has been transferred into a solvent which is miscible with water. The disadvantage of this procedure is that the active ingredients are present to a higher or lower extent in the oil phase, thus reducing the yield.

Furthermore, it is known that an aqueous extract of neem kernels may be used to isolate the azadirachtin-containing effective substance by extraction with methyl-tertiary-butylether. After this the methyl-tertiary-butylether is evaporated and the residue dissolved in methanol. Subsequently, the methanolic solution is extracted with petrolether and concentrated by evaporation. In relation to the neem kernels, a yield of 0.8% of a biologically active product is obtained in this manner. Such a method is economically not feasible.

OBJECT OF THE INVENTION

The present invention has the aim to propose an economically sound and, consequently, inexpensive method, which is technically simple and allows high yields of an azadirachtin-rich insecticide with low oil content.

DESCRIPTION OF THE INVENTION

According to the invention, the neem kernels are first reduced to small pieces and water is added as the solvent. This first extraction step of azadirachtin from the kernels can be repeated several times with fresh water until 90% or more of the active substance is removed from the ground residues. After this first extraction step, the active ingredients should be extracted from the aqueous solution. This may be achieved in two ways.

In the first way, a non-aqueous solvent, which is not miscible with Water in all ratios, and has a better solubility for azadirachtin than water itself, is added to the aqueous solution of the active substance. After mixing and absorption of the azadirachtin by the non-aqueous phase, the phases are allowed to separate. This way of isolation of azadirachtin using at first an aqueous solution has the advantage that unwanted oil is hardly present in the azadirachtin-rich phase and does not have to be removed in later steps of the process. After phase separation is complete, the azadirachtin-rich phase is concentrated and the concentrate is added and mixed with a 1- to 20-fold volume of a liquid hydrocarbon. As the product, an azadirachtin-rich precipitate forms at the bottom, which may be taken and dried. With this process, a powdery concentrate of the active substance with a very long storage stability is obtained.

In the second method corresponding to the invention, a surfactant with a turbidity temperature, which favorably lies between 20° and 80° C., is added to the azadirachtin-containing aqueous solution. This surfactant has a higher solubility for azadirachtin than water, so that the azadirachtin-rich surfactant phase may be separated after increasing the temperature above the turbidity temperature. The obtained concentrate of the active ingredients can be used directly, after dilution with water, or can be stored for several months for future use.

Examples for the process described by the invention are described in the following.

Both methods described in detail below are based on the use of water as the primary extracting solvent. Firstly, the neem kernels of the dried neem fruits are ground (for example with a meat-chopper containing a disc with holes of 3 to 8 mm diameter on the average). At room temperature, the ground material obtained is stirred into the 2- to 20-fold amount (favorably in such a manner that the solid residue of the ground material comprises 30 to 50% of the total system; for sedimentation this usually corresponds to a 6- to 10-fold amount of water, for centrifugation for example, only an addition of water in the 3- to 5-fold amount of ground neem kernels is necessary) of water. The system is then repeatedly stirred at intervals of approximately ½ hour for about 3 to 12 hours (or more; the partition equilibrium of azadirachtin between the ground kernels and the aqueous solution is closely reached after about 5 hours; raising the temperature up to 70° C. increases the adjustment of the partition equilibrium slightly) and then left alone for a few hours for the sedimentation of the residues. The separation of the possibly slightly turbid aqueous phase from the solid residues can be achieved by different physical processes like filtration, sedimentation, centrifugation.

In order to increase the yield, the extraction of the residue with water can be repeated. Usually about more than 90% of the azadirachtin present is dissolved in the aqueous phase after 2 to 3 extractions. The aqueous solutions (extracts) may be combined for further working up.

Extraction by Solvent

A solvent, which is not completely miscible with water, such as a ketone like butanone, pentanone or hexanone, an alcohol such as 1-butanol or pentanol, an ester such as ethylacetate or butylacetate or a halogenatedhydrocarbon such as di- or tri-chloromethane, is mixed with the aqueous extract in a ratio of solvent:water≈1.10 and then left standing for some hours until the unmiscible phases have separated (about 5 to 30 hours). The non-aqueous phase is then taken and concentrated to ⅕ to ¹⁄₁₀ of its volume. The obtained concentrate is then slowly mixed with approximately a 2- to 20-fold volume of a liquid hydrocarbon such as hexane or petrolether whereupon a white to slightly yellowish precipitate is formed. After some minutes, the precipitate has sedimented to the bottom of the vessel and the nonpolar liquid solution can easily be decanted. After drying of the precipitate, the azadirachtin content is usually between 30 to 60%, with a total yield of 80 to 95% of the azadirachtin content of the neem kernels used. The insecticidal activity of the product equals that of pure azadirachtin since many of the other extracted compounds of the neem kernels presumably exhibit insecticidal activity to varying degrees as well.

Extraction by Surfactant

The aqueous extract is mixed at room temperature with 1 to 10%, preferably about 5%, of a surfactant with a turbidity temperature between approximately 20 to 80° C., such as p-tertiary-octylphenol-5,7-glycolether, p-tertiary-octylphenol-8-10-glycolether, oleicacidamide-heptaglycolether, dodecanolheptaglycolether or p-iso-nonylphenoldecaglycolether, and subsequently the solution is warmed until the temperature has increased, usually about 5° C., above the turbidity temperature of the surfactant. After a short time, the surfactant and azadirachtin-rich (lower) phase formed can be separated and used directly as an anti-insect concentrate.

EXAMPLE 1

Extraction with Ethylacetate 1 kg neem kernels are reduced to small pieces using a meat-mincer containing a disc with holes of about 4 mm diameter and then stirred into 2.5 liters of water at 30° C. After standing for 10 hours, the aqueous phase is decanted from the ground residue. The ground residue is pressed through a linen cloth in order to obtain further amounts of the aqueous solution. The combined aqueous solutions (1.9 liter) is mixed thoroughly with 250 ml ethylacetate and left standing for 6 hours at room temperature. After this, the upper ester rich phase (about 150 ml) is separated and another 200 ml of ethylacetate is mixed with the aqueous phase. After 4 hours, the second ester phase is separated and the extraction with 200 ml ethylacetate is repeated. The combined three ester phases (about 500 ml in total) are concentrated in vacuo to ¹⁄₁₀ of their volume at approximately 45° C. Immediately afterwards, the warm residue of the distillation is stirred into 400 ml petrolether during which the azadirachtin-containing active substance precipitates and is totally sedimented to the bottom after about 30 minutes. The liquid layer is decanted and the precipitate is whirled up in another 20 ml of petrolether. After centrifugation, the sediment is dried for 12 hours at 30° C. yielding 4.61 g of a slightly yellowish powder with an azadirachtin content of 44% according to HPLC-analysis.

After two repetitions of the extraction of the ground neem kernel residue with water and subsequently of the aqueous solution with ethylacetate, 0.87 g and 0.58 g of powdery crude azadirachtin are obtained with azadirachtin contents of 35 and 41%. Consequently, the total yield of the extraction is 6.06 g of a slightly yellowish powder containing 2.6 g of azadirachtin. The analysis of the azadirachtin content of the neem kernels used gave 2.9 g azadirachtin/kg kernels. Thus the total yield of azadirachtin was 90%.

EXAMPLE 2

Extraction with a Surfactant 5 kg neem kernels are reduced to small pieces using a meat-mincer containing a disc with holes of about 6 mm diameter and then stirred into 70 liters of water at 20° C. After standing for 10 hours, the upper aqueous phase (45 l) is decanted from the ground residue phase (35 l) into a 60 l barrel with a cock at the bottom and therein mixed thoroughly with 1.45 l p-tertiary-octylphenol-5,7-glycolether at 18° C.

With the help of a PVC-tube (15 m long; 2 cm outer diameter), which is rolled up in the 60 l barrel and connected to a circulation thermostat (adjusted to 75° C.), the mixture (aqueous extract and surfactant) is heated to 63° C. within 3 hours. The surfactant-rich phase gathering at the bottom is mixed every 30 minutes with the aqueous solution by stirring. After a temperature of 63° C. is reached, the solution may rest for approximately 30 minutes and then the lower phase (5.5 l) is drained. The azadirachtin content of the upper and lower phase amounts to 2.7 and 5.4 g, respectively. For the surfactant-rich phase, this corresponds to an azadirachtin concentration of 1 g/l. For example, after dilution with water in the ratio 1:10 to 1:100, this solution may be used as an insecticide directly. Higher yields are obtained by repetition of the phase separation with a new surfactant or an increase in surfactant concentration at the beginning. For this procedure, it is reasonable to have the possibility of adjusting the turbidity temperature in a possibly wide temperature range. This is possible for example using mixtures of different surfactants, such as p-tertiary-octylphenol-5,7-glycolether and p-tertiary-octylphenol-8-10-glycolether. For these two substances, a closely linear relation between their concentration and their turbidity temperature is found.

I claim:

1. A method of recovering azadirachtin from seed kernels of the neem tree comprising the steps of: grinding the seed kernels to produce a pulverized component; extracting azadirachtin from the pulverized component using water alone as a solvent to obtain an azadirachtin-containing aqueous solution; adding a nonaqueous solvent which is not completely miscible with water and has a higher solubility for azadirachtin than water to the azadirachtin-containing aqueous solution to extract the azadirachtin from the azadirachtin-containing aqueous solution and obtain an azadirachtin-containing solution; recovering the azadirachtin-containing solution; concentrating the azadirachtin-containing solution to produce an azadirachtin concentrate; adding said azadirachtin concentrate to a liquid hydrocarbon to form an azadirachtin precipitate; and recovering said azadirachtin precipitate.

2. The method of claim 1, wherein the pulverized component has a particle size of 0.1 to 2 mm.

3. The method of claim 1, wherein the grinding is carried out with a mincer containing a disk with hole diameters of 3 to 8 mm.

4. The method of claim 1, wherein a 1- to 20-fold volume amount of water, based on the pulverized component, is added to the pulverized component.

5. The method of claim 4, wherein the water has a temperature of approximately 20° C.

6. The method of claim 5, wherein the extraction of the azadirachtin with water is carried out for a period of approximately 5 hours and the temperature of the system is raised gradually up to 70° C.

7. The method of claim 6, wherein the aqueous solution is stirred at intervals of approximately 30 minutes and then is left standing for about 1 to 3 hours for sedimentation.

8. The method of claim 1, wherein the extraction is repeated with fresh water until about 90% of the azadirachtin is present in the aqueous solution.

9. The method of claim 1, wherein the non-aqueous solvent is selected from the group consisting of a ketone, an alcohol, an ester and a halogenated hydrocarbon.

10. The method of claim 1, wherein the volume ratio of non-aqueous solvent:water is about 1:10.

11. The method of claim 1, wherein the non-aqueous solvent is added while stirring the aqueous solution and then left standing for several hours until non-miscible phases have separated.

12. The method of claim 10, wherein the azadirachtin-containing solution is concentrated to ⅕ to ⅒ of its volume and the concentrate obtained is mixed with a 1- to 20-fold volume amount of liquid hydrocarbon and the obtained precipitate is recovered from the solution by pouring it off and the azadirachtin precipitate subsequently dried.

13. The method of claim 1, wherein the dried azadirachtin precipitate itself, or after formulation with at least one of an emulsifier and a solvent, is used as an insecticide.

14. A method of recovering azadirachtin from seed kernels of the neem tree comprising the steps of: grinding the seed kernels to produce a pulverized component; extracting azadirachtin from the pulverized component using water alone as a solvent to obtain an azadirachtin-containing aqueous solution; adding a surfactant having a turbidity temperature from 20°–80° C. and a higher solubility for azadirachtin than water to the azadirachtin-containing aqueous solution to form a resultant mixture; raising the temperature of the resultant mixture to greater than the turbidity temperature to form an azadirachtin-rich surfactant phase, and recovering the azadirachtin-rich surfactant phase.

15. The method of claim 14, wherein the surfactant is selected from the group consisting of p-tertiary-octylphenol-5,7-glycolether, p-tertiary-octylphenol-8-10-glycolether, oleicacidamide-heptaglycolether, dodecylalcoholheptaglycol-ether, p-isononylphenoldecaglycolether, and mixtures thereof.

16. The method of claim 14, wherein the temperature of the resultant mixture is raised approximately 5° C. above the turbidity temperature.

17. The method of claim 14, wherein at least one of an emulsifier and water is added to the azadirachtin-rich surfactant phase to form a formulation.

18. The method of claim 17, wherein water is added to the azadirachtin-rich surfactant phase in the ratio of approximately 1:100.

19. The method of claim 14, wherein the surfactant is a mixture of p-tertiary-octylphenol-5,7-glycolether and p-tertiary-octylphenol-8-10-glycolether.

* * * * *

UNITED STATES PATENT AND TRADEMARK OFFICE
CERTIFICATE OF CORRECTION

PATENT NO. : 5,695,763
DATED : December 9, 1997
INVENTOR(S) : Hubertus KLEEBERG

It is certified that error appears in the above-indentified patent and that said Letters Patent is hereby corrected as shown below:

On the title page, please correct the Assignee's name as follows:

---Trifolio-M GmbH, Herstellung und Vertrieb hochreiner Biosubstanzen---.

Signed and Sealed this

Seventh Day of July, 1998

Attest:

BRUCE LEHMAN

Attesting Officer         Commissioner of Patents and Trademarks